US00PP25438P2

(12) United States Plant Patent
Renault

(10) Patent No.: US PP25,438 P2
(45) Date of Patent: Apr. 14, 2015

(54) ***HYDRANGEA* PLANT NAMED 'RENSUN'**

(50) Latin Name: *Hydrangea paniculata*
Varietal Denomination: RENSUN

(71) Applicant: Jean Renault, Gorron (FR)

(72) Inventor: Jean Renault, Gorron (FR)

( * ) Notice: Subject to any disclaimer, the term of this patent is extended or adjusted under 35 U.S.C. 154(b) by 186 days.

(21) Appl. No.: 13/694,363

(22) Filed: Nov. 26, 2012

Related U.S. Application Data

(60) Provisional application No. 61/632,789, filed on Jan. 31, 2012.

(51) Int. Cl.
*A01H 5/00* (2006.01)

(52) U.S. Cl.
USPC ..... Plt./250

(58) Field of Classification Search
CPC ..... A01H 5/02; A01H 5/00; A01H 1/02
USPC ..... Plt./250
See application file for complete search history.

(56) References Cited

PUBLICATIONS

Houtman. Plantarium 2010 Dendroflora nr 47 2010, pp. 103-114.*
English translation of Dendroflora No. 47 2010, p. 8 of Houtman p. 110.*

* cited by examiner

*Primary Examiner* — June Hwu
(74) *Attorney, Agent, or Firm* — Penny J. Aguirre

(57) ABSTRACT

A new cultivar of *Hydrangea paniculata* named 'RENSUN', characterized by its panicles of flowers of primarily sterile flowers that emerge white in mid summer and change to pink as they mature with the combination of white and pink panicles providing a multicolor effect, its reddish-brown flowering stems, and its uniform and compact plant habit with good suitability for planting in small spaces and containers.

2 Drawing Sheets

Genus/species: *Hydrangea paniculata.*
Varietal denomination: 'RENSUN'.

BACKGROUND OF THE INVENTION

The present invention relates to a new and distinct cultivar of *Hydrangea paniculata* and will be referred to hereafter by its cultivar name, 'RENSUN'. 'RENSUN' represents a new deciduous shrub grown for landscape use.

The new *Hydrangea* resulted from a controlled breeding program that commenced in 1987 in Gorron, France. 'RENSUN' was selected as a whole plant mutation in a seedling plot in the ground in Gorron, France in 2005. The parents of 'RENSUN' were unnamed proprietary seedlings that arose after a multiple series of crosses.

Asexual reproduction of the new cultivar was first accomplished by softwood cuttings in May of 2006 by the Inventor in Gorron, France. The characteristics of this cultivar have been determined to be stable and are reproduced true to type in successive generations.

SUMMARY OF THE INVENTION

The following traits have been repeatedly observed and represent the characteristics of the new cultivar as observed on plant grown in Gorron, France. These attributes in combination distinguish in 'RENSUN' from other varieties of *Hydrangea* known to the Inventor.

1. 'RENSUN' blooms with panicles of flowers that emerge white in mid summer and change to pink as they mature, the combination of white and pink panicles provide a multicolor effect.

2. 'RENSUN' exhibits a uniform and compact plant habit with good suitability for planting in small spaces and containers.
3. 'RENSUN' exhibits reddish-brown flowering stems.
4. 'RENSUN' exhibits primarily sterile flowers as fertile flowers are rarely produced.

Comparison to other *Hydrangea paniculata* cultivars:

'Unique' (not patented) is similar to 'RENSUN' in having white flowers that turn pink but differs from 'RENSUN' in having more fertile flowers, and in having a more erect and less compact plant habit. 'DVPpinky' (U.S. Plant Pat. No. 16,166) is similar to 'RENSUN' in having flowers that are white in color and turn pink, however 'DVPpinky' differs from 'RENSUN' having a more erect plant habit and in having flowers that the pink coloration exists for a very short time before turning red, and also in having more fertile flowers. 'RENHY' (U.S. Plant Pat. No. 20,670) is similar to 'RENSUN' in having white flowers that turn to pink and in lacking fertile flowers, however 'RENHY' differs from 'RENSUN' in having flowers that subsequently change to red or burgundy and in having a less compact plant habit.

BRIEF DESCRIPTION OF THE DRAWINGS

The drawings presented are digital photographs taken of plants 3 years in age in Gorron, France.

The photograph in FIG. 1 provides a view of the plant habit of 'RENSUN' in bloom as grown in a 2-gallon container.

Figure 1:
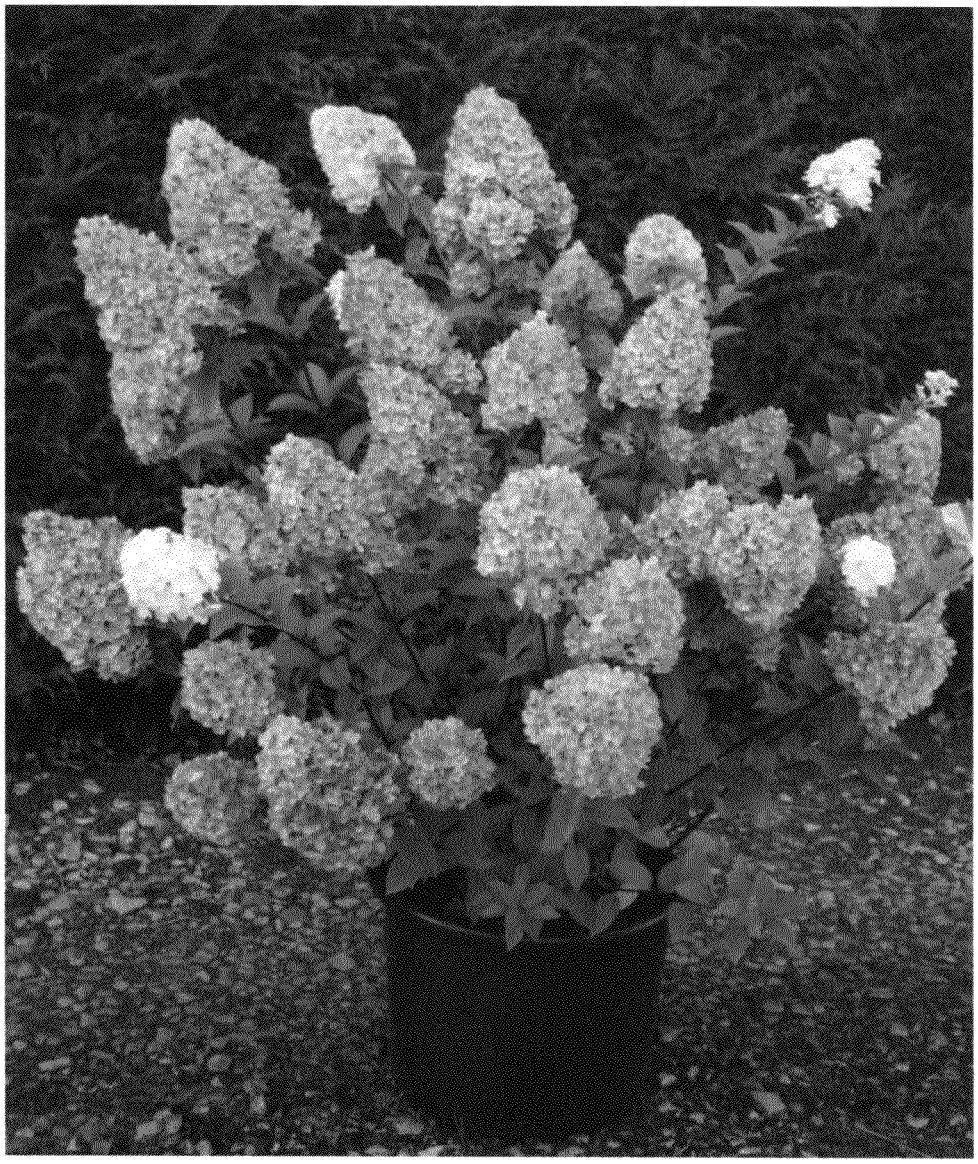
Figure 2:
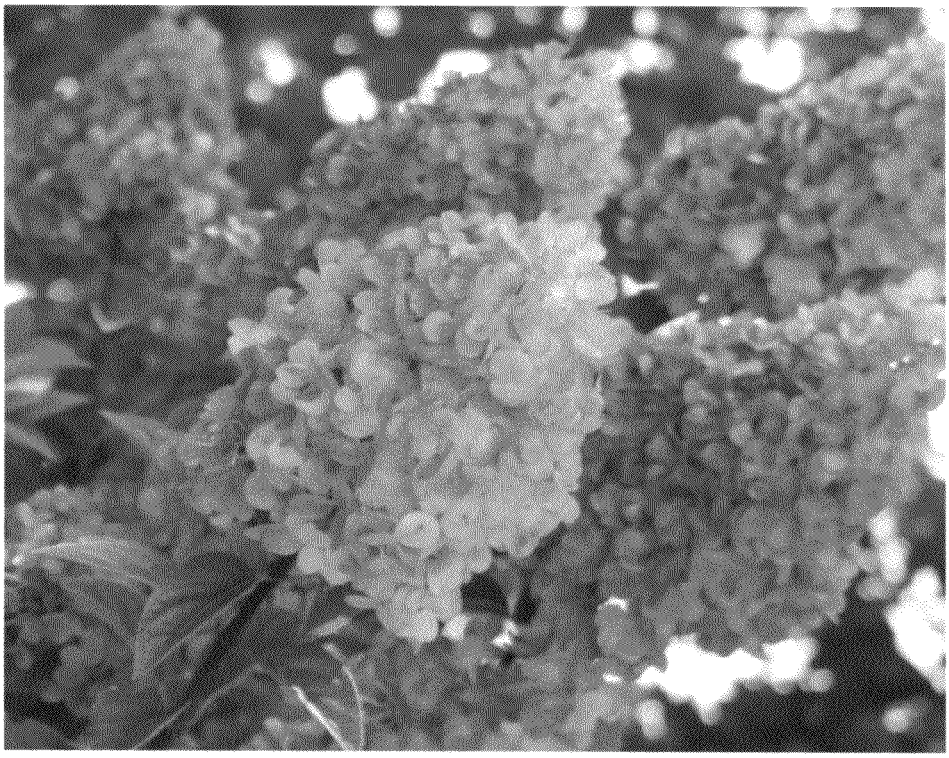

The photograph in FIG. 2 provides a close-up view of inflorescences of 'RENSUN'.

Figure 3:
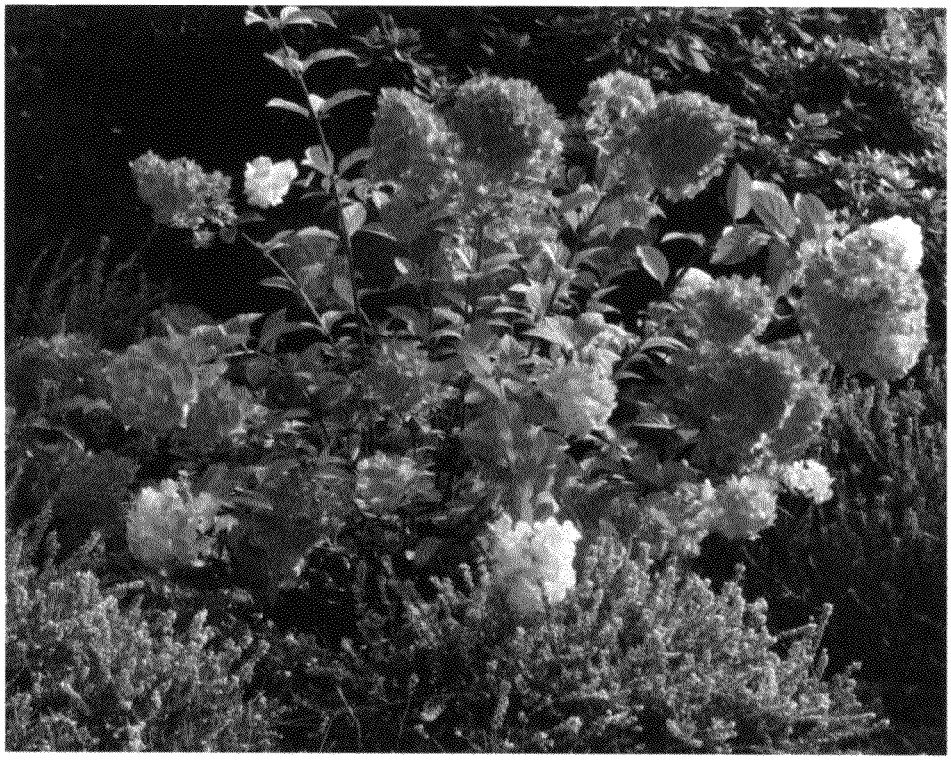

The photograph in FIG. 3 provides a close-up view of a plant of 'RENSUN' grown in a garden.

The colors in the photographs are as close as possible with the photographic and printing technology utilized. The color values cited in the detailed botanical description accurately describe the colors of the new *Hydrangea*.

BOTANICAL DESCRIPTION OF THE PLANT

The following is a detailed description of the new cultivar as observed on 3 year-old plants as grown outdoors in Gorron, France and of plants two years in age as grown under greenhouse conditions in St. Paul, Minn. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—From mid July to mid October in France.

*Plant habit*.—Erect through mid summer, becoming supple and cascading in late summer through fall.

*Height and spread*.—Reaches 1 to 1.3 m in height and 1 to 1.2 m width.

*Cold hardiness*.—U.S.D.A. Zone 4.

*Diseases and pests*.—No susceptibility or resistance to diseases or pests has been observed.

*Root description*.—Fibrous.

Growth and propagation:

*Propagation*.—Softwood stem cuttings.

*Root initiation*.—About 2 weeks in summer under greenhouse conditions without supplemental lighting and about 3 weeks in winter with bottom heat in France.

*Time required to produce a salable crop*.—A plug of a rooted cutting finishes in a P9 container grown outdoors in about 5 to 6 months.

Stem description:

*Shape shape*.—Round, solid.

*Stem color*.—New wood 59B, mature wood 165A, old wood (dormant); 199C.

*Stem diameter*.—Average of 5 mm on average.

*Stem surface*.—Pubescent when young becoming glabrous.

*Internode length*.—Average of 3 cm.

*Branching*.—A single dormant stem will produce an average of 5 primary branches. Subsequent branching is determined by pinching.

Foliage description:

*Leaf shape*.—Elliptic.

*Leaf division*.—Simple.

*Leaf base*.—Cuneate.

*Leaf apex*.—Primarily acuminate.

*Leaf venation*.—Pinnate, recessed, color 149C on upper surface and 144D on lower surface.

*Leaf margins*.—Serrated.

*Leaf attachment*.—Petiolate.

*Leaf arrangement*.—Opposite.

*Leaf surface*.—Glabrous on upper and lower surface.

*Leaf color*.—Newly formed leaves upper surface; 137C, newly formed leaves lower surface; 138B, mature leaves upper surface; 137A to 139A, mature leaves lower surface; 138A, fall color upper and lower surface; 199D.

*Petioles*.—Average of 1.5 cm in length and 2.5 mm in width, sulcate in shape, stipules absent, 59B in color.

Flower description:

*Inflorescence type*.—Broadly pyramidal panicles of sterile flowers.

*Lastingness of inflorescence*.—Persistent but color is retained for 4 to 6 weeks before browning.

*Inflorescence size*.—Average of 12 cm in diameter and 15 cm in length.

*Inflorescence number*.—One per stem, new shoots develop throughout the summer.

*Flower number*.—Numerous, approximately 400 per inflorescence.

*Fragrance*.—None.

*Flower buds*.—Up to 6 mm in length and 4 mm in width prior to opening, color is 145B changing to 145C prior to opening.

*Peduncles*.—Average of 4 cm in length and 4.5 mm in width, 59B in color, surface is glabrous.

*Bracts*.—Not observed.

*Pedicels*.—8 to 12 mm in length and 1 mm in width, color is 145D flushed with 63C at peak bloom, surface is glabrous.

*Flower size*.—Average of 3.2 cm in diameter and 1 cm in depth.

*Sepals*.—4, orbicular, aposepalous, partially overlapping, rounded apex, cuneate base, entire margin, average of 1.5 cm in length and 1.4 cm in width, glabrous on both surfaces, color upper and lower surface; 155A when opening with some flushed with 63C to 63D, changes to 63A to 63C mottled with 155A and 145D, dry and fade to about 161B.

*Center (eye) size*.—2 mm in diameter, color is 155A when flowers first open changing 145D at maturity.

*Reproductive organs*.—None, fertile flowers are very rarely produced and not observed on the plant available for data collection.

It is claimed:

1. A new and distinct cultivar of *Hydrangea* plant named 'RENSUN' as herein illustrated and described.

* * * * *